(12) United States Patent
Decosterd et al.

(10) Patent No.: US 6,755,650 B2
(45) Date of Patent: Jun. 29, 2004

(54) DENTAL APPARATUS

(75) Inventors: Christian Decosterd, Vinzel (CH); Lutz Beerstecher, Borex (CH)

(73) Assignee: Ferton Holding S.A. (CH)

( * ) Notice: Subject to any disclaimer, the term of this patent is extended or adjusted under 35 U.S.C. 154(b) by 93 days.

(21) Appl. No.: 10/104,596

(22) Filed: Mar. 21, 2002

(65) Prior Publication Data

US 2003/0077552 A1 Apr. 24, 2003

(30) Foreign Application Priority Data

Mar. 23, 2001  (DE) ......................................... 101 14 331

(51) Int. Cl.⁷ ............................. A61C 3/02; A47J 31/00
(52) U.S. Cl. ........................ 433/88; 433/80; 222/185.1
(58) Field of Search .............................. 433/80, 84, 88; 222/402.17, 185.1; 215/307, 309, 310, 311, 312, 315; 601/162, 165, 155; 604/91, 83

(56) References Cited

U.S. PATENT DOCUMENTS

| | | | |
|---|---|---|---|
| 3,871,560 A | * | 3/1975 | Crippa ....................... 222/185 |
| 4,492,575 A | | 1/1985 | Mabille |
| 4,770,632 A | * | 9/1988 | Ryder et al. ................... 433/28 |
| 4,824,368 A | * | 4/1989 | Hickman ...................... 433/80 |
| 4,830,210 A | | 5/1989 | Mabille |
| 5,577,638 A | * | 11/1996 | Takagawa ................ 222/185.1 |
| 5,927,977 A | * | 7/1999 | Sale et al. .................... 433/86 |
| 6,485,304 B2 | * | 11/2002 | Beerstecher et al. .......... 433/88 |

* cited by examiner

Primary Examiner—Cary E. O'Connor
(74) Attorney, Agent, or Firm—Ostrolenk, Faber, Gerb & Soffen, LLP

(57) ABSTRACT

A dental apparatus comprises a connector arrangement for allowing a connection of a fluid reservoir containing a fluid which is supplied to a dental handpiece under control of a valve arrangement by a suction pump which has a suction line that is connected with a reception member of a connector piece of the fluid reservoir on which a closure one-way check valve is arranged which is biased by a closure spring towards a closing position on a valve seat of the connector piece which is further provided with an aeration one-way check valve over an aeration opening for compensating a negative pressure which will be produced inside of the fluid reservoir when the closure one-way check valve is opened at its valve member and fluid is drawn from the fluid reservoir for being supplied to the handpiece.

14 Claims, 2 Drawing Sheets

DENTAL APPARATUS

FIELD OF THE INVENTION

The present invention relates to a dental apparatus comprising means for allowing a connection of a fluid reservoir containing a fluid which is supplied to a dental handpiece under control of a valve arrangement by a suction pump which has a suction line that is connected with a reception member of a connector piece of the fluid reservoir.

The invention equally relates to a fluid reservoir containing a fluid which is intended for being used with a dental apparatus and for being supplied to an associated handpiece for use with a dental treatment.

BACKGROUND OF THE INVENTION

A prior art dental apparatus of the kind as herein referred is described in U.S. Pat. No. 4,830,210. For allowing a connection of a fluid reservoir a closure means of the same comprises at least two closure disks that are provided with at least one discharge opening at a common off-center position so that only in a singular relative turning position of these two closure disks a discharge of the fluid will be allowed. This definite turning position is obtained by a fitting which is adapted for being fastened to a neck portion of the fluid reservoir by means of a turn-lock fastener which has a discharge tube at a corresponding off-center position. By an interaction of this discharge tube with the discharge opening of the one closure disk the same may be turned into a position in which the discharge tube will be axially aligned with the discharge openings of the two closure disks. Since the discharge tube of the fitting is also provided with a check valve that opens in the discharge direction of the fluid the fitting may be used as a connector piece of the fluid reservoir with the dental apparatus for allowing supply of fluid to an interconnected handpiece under either a positive or a negative pressure of a pump which is installed inside of a housing of the dental apparatus. The fitting is fixed on an upper wall of the housing and presents a screw-connection with the neck portion of the reservoir. For compensating a negative pressure which will exist inside of the fluid reservoir when fluid is withdrawn for being supplied to the handpiece a complementing provision is made for supplying the fluid reservoir with compressed air via a second check valve of a second discharge tube. This second discharge tube is axially aligned with a pair of second openings of the two closure disks in the definite turning position for supplying compressed air to the inside of the fluid reservoir while fluid is withdrawn via the check valve of the first discharge tube and its associated discharge openings of the two closure disks whereby the two check valves of the two discharge tubes are opened in opposite directions.

SUMMARY OF THE INVENTION

An object of the present invention is to provide a dental apparatus comprising less complicated means for allowing a connection of a fluid reservoir and presenting at the same time a less complicated functional sequence in respect to the supply of fluid to an associated dental handpiece under the control of a valve arrangement.

It is a further object of the present invention to provide a fluid reservoir containing a fluid for being used with a dental apparatus connected with a dental handpiece for dental treatment which equally meets the demand for a less complicated connection of the fluid reservoir with a dental apparatus which has a suction pump by means of which the fluid of the fluid reservoir may be supplied to an associated dental handpiece under control of a valve arrangement.

The present invention accordingly provides a dental apparatus as well as a fluid reservoir for use with a dental apparatus which are each characterised by the features as outlined in the related claims.

A dental apparatus in accordance with the present invention therefore provides means which allow a very easy and at the same time safe-proof connection of a fluid reservoir for supplying the fluid which is contained in the fluid reservoir to an associated dental handpiece under control of two one-way check valves one of which is a closure valve and the other is an aeration valve. The connecting means including these two one-way check valves may be manufactured with low costs and may be easily handled especially when comprising a plug-in connection of a connector piece of the fluid reservoir and a reception member which will be arranged on a housing of the dental apparatus so that with such a structure and with such a possibility for a low-cost manufacturing of the fluid reservoir the possibility will exist for offering the fluid reservoir as a non-return product which may contain a variety of different fluids for a dental treatment.

Other objects, features and advantages of the present invention will become apparent from reading the following description of a preferred embodiment of a dental apparatus and a fluid reservoir according to the present invention.

DETAILED DESCRIPTION

Figure 1:
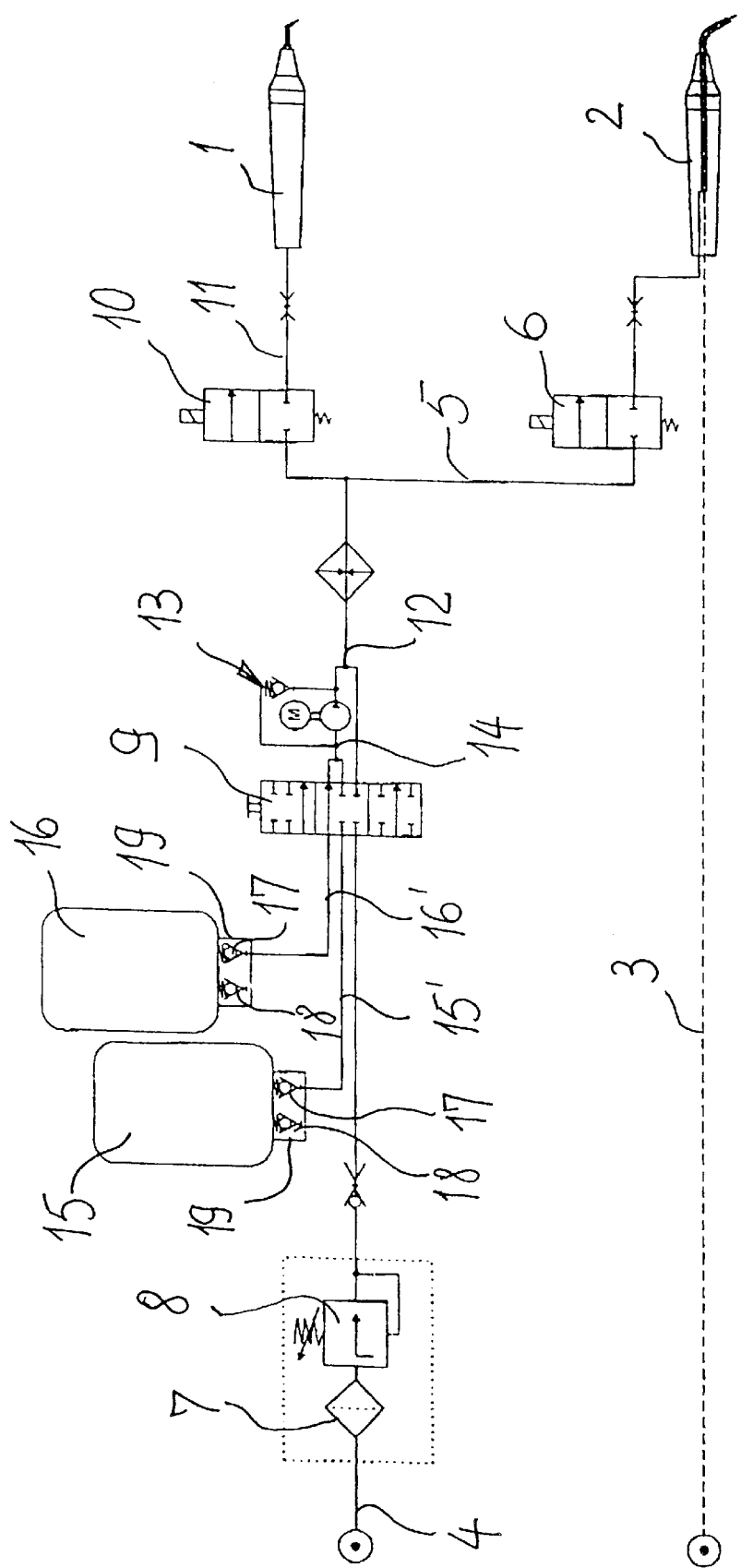
FIG. 1 is a diagrammatic view of a dental apparatus incorporating a connecting system for a fluid reservoir in accordance with the present invention.
Figure 2:
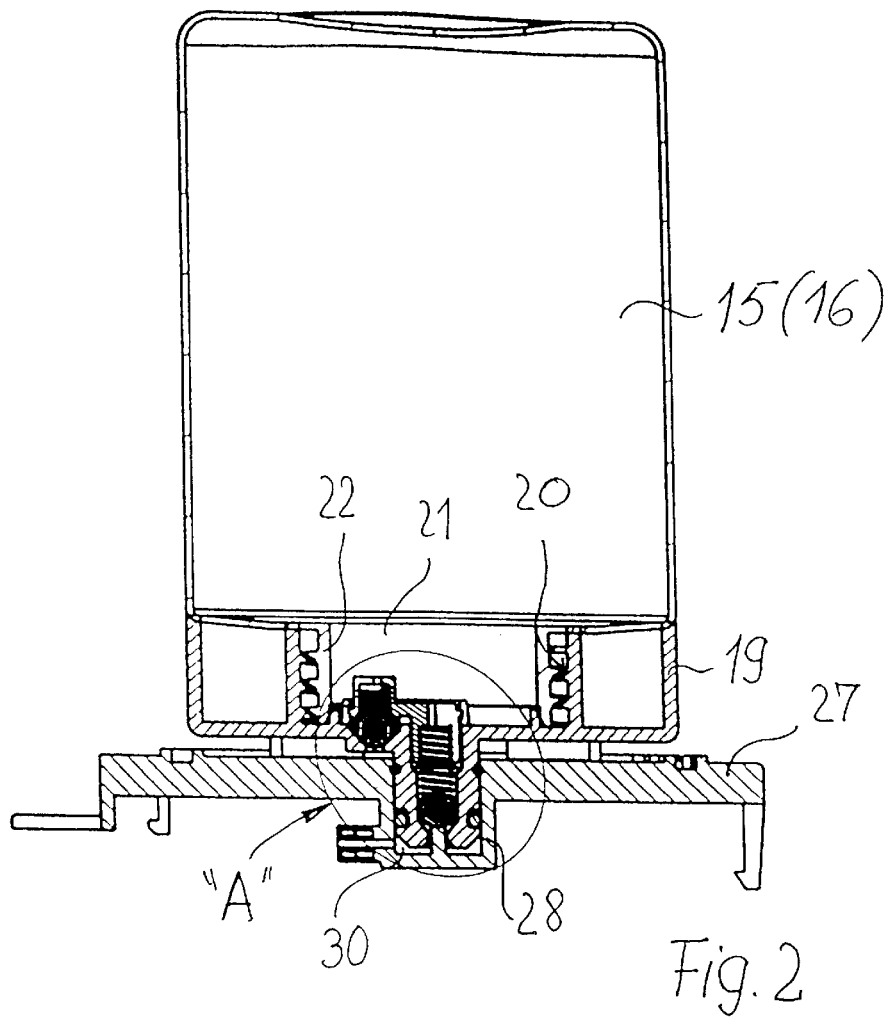
FIG. 2 is a sectional view of the connecting system according to a preferred embodiment of the present invention.
Figure 3:
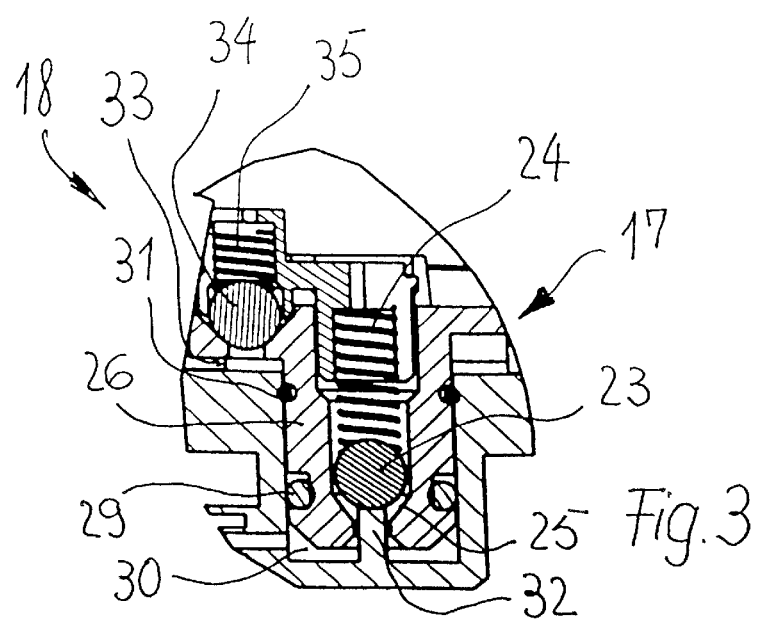
FIG. 3 is an enlarged view of the detail A in FIG. 2.

A dental apparatus of the kind as envisaged by the present invention could be basically designed in the same manner as the dental abrasive blasting apparatus according to the U.S. Pat. No. 4,492,575 to which reference may therefore be made for further details of the following description.

The dental apparatus is designed with two interconnected handpieces 1 and 2 of which the one handpiece 1 is a scaler by which an ultrasonic treatment of the teeth may be practised. The second handpiece 2 is an abrasive blasting instrument which has an integrated powder reservoir. The second handpiece 2 is connected with an associated supply line 3 for compressed air for supplying a nozzle piece at a tip portion of the handpiece 2 with a combined jet of compressed air mixed with an abrasive dental powder which is contained in the integrated powder reservoir. Water is also supplied via an associated water supply line 4 which connects to a branch line 5 via a change-over switch valve 6 to a connecting line of the second handpiece 2.

The water supply line 4 has a serially connected filter 7, a pressure regulator 8 and a directional control valve 9 which is connected through branch line 5 with another change-over switch valve 10 connecting to a connecting line 11 of the one handpiece 1. The connecting line 11 may alternatively be connected by its change-over switch valve 10 with a pressure line 12 of a suction pump 13 which by its suction line 14 is connected with the directional control valve 9 that is arranged upstream of the suction pump 13 and further also upstream of the two change-over switch valves 6 and 10 which are connected in parallel with the branch line 5 for alternately connecting to the two handpieces 1 and 2. The suction line 14 of the suction pump 13 may alternatively be connected by the directional control valve 9 with a first fluid reservoir 15 and a second fluid reservoir 16. The connecting lines 15' and 16' of these two fluid reservoirs 15 and 16 connect with two different control positions of the directional control valve 9 to the suction line 14 of the suction pump 13. With a respective control position of the change-over switch valve 10 when actuated separately from the change-over switch valve 6 the connecting line 11 of the handpiece 1 may be supplied either with fresh water from the interconnected water supply line 4 or with fluid from either of the two fluid reservoirs 15 and 16 dependent upon which one of the two connecting lines 15' and 16' will be connected via the directional control valve 9 with the suction line 14 of the suction pump 13 and further through pressure line 12 of the suction pump to the branch line 5 connecting to the two change-over switch valves.

The two fluid reservoirs 15 and 16 are each provided with two one-way check valves 17 and 18 which are arranged on a cap-shaped cover piece 19. Each cap-shaped cover piece 19 is provided with a screw-type closure means 20 which at a position of a filler opening 21 allows a screw-connection with a neck portion 22 of the fluid reservoir. The screw-type closure means 20 is formed with an inner thread on the cap-shaped cover piece 19 and a complementary outer thread on the neck portion 22 of the fluid reservoir.

As may be further noted the two one-way check valves 17 and 18 are each formed as ball check valves. The valve ball 23 of one-way check valve 17 is biased by a closure spring 24 against a valve seat 25 which is formed with a bore of a spigot-like connection piece 26 at a position opposite to the screw-type closure means 20 of the cap-shaped cover piece 19. The spigot-like connection piece 26 is arranged for allowing a plug-in connection of the cap-shaped cover piece 19 with a complementary cup-shaped recess in an upper wall 27 of the housing of the dental apparatus. The cup-shaped recess forms a reception member 28 which provides a fixed connection for a respective fluid reservoir. The plug-in connection is sealed by a packing ring 29 which seals a clearance 30 at the bottom of the recess to which the connecting lines 15' and 16' of the two fluid reservoirs 15 and 16 are connected. It is further secured by a spring ring 31 for also maintaining the clearance 30 for a perfect connection of an associated connecting line with an interconnected fluid reservoir. The reception member 28 is further provided with a projection 32 which protrudes upwardly from the bottom of the recess to thereby provide a counter part for pushing the valve ball 23 into an open position against the biasing force of its closure spring 24 in the plug-in connecting position of the fluid reservoir. The associated connecting line 15' and 16' will accordingly be provided with an open connection with the associated fluid reservoir 15 or 16 so that fluid may be withdrawn from the fluid reservoir whenever the suction pump 13 will be switched-on for supplying fluid from either of the two fluid reservoirs to the connecting line of the associated handpiece.

The cap-shaped cover piece 19 is further provided with an aeration opening 33 which is closed by a valve ball 34 of the second one-way check valve 18 under the action of a closure spring 35. The aeration opening 33 connects to an air gap existing between the cap-shaped cover piece 19 and the upper wall 27 of the housing of the dental apparatus so that when a negative pressure will exist inside of the fluid reservoir whenever fluid is supplied to an associated handpiece via the associated suction line of the suction pump a compensation of this negative pressure will be ruled by an opening of the valve ball 34 against the biasing force of its closure spring.

When all of the fluid of any fluid reservoir 15, 16 is consumed it will then only be necessary to take off the empty fluid reservoir from the reception member 28 and to replace the same by a new fluid reservoir being filled with the same or with a different fluid. Such a replacement may be easily handled especially in such a case where the fluid reservoirs are exemplified as non-return products incorporating already the two one-way check valves on a respective cap-shaped cover piece. If such a cap-shaped cover piece with the two one-way check valves will not be provided for such non-return products this will then on the other hand only necessitate a removal of the cap-shaped cover piece from an empty fluid reservoir for obtaining a screw connection with a threaded neck portion of a full-filled replacement fluid reservoir after a normally provided closure cap of the same has been removed.

We claim:

1. A dental apparatus comprising a connector arrangement for allowing a connection of a fluid reservoir containing a fluid which is supplied to a dental handpiece under control of a valve arrangement by a suction pump which has a suction line that is connected with a reception member of a connector piece of the fluid reservoir, comprising:

a closure one-way check valve which is arranged on the connector piece of the fluid reservoir whereby a valve member which is biased by a closure spring towards a closing position on a valve seat of the connector piece may be pushed by a counterpart into an open position against the biasing force of the closure spring, and an areation one-way check valve which is arranged over an aeration opening of the connector piece of the fluid reservoir for compensating a negative pressure which will be produced inside of a fluid reservoir when the closure one-way check valve is opened at its valve member and fluid is drawn from the fluid reservoir via the suction line of the suction pump and supplied to the handpiece via a pressure line of the suction pump, said closure one-way check valve and said aeration one-way check valve being both arranged on a cap-shaped cover piece which for closing a fluid filler opening of the fluid reservoir may be fixed on its one side to the fluid reservoir and which on its opposite side is provided with a spigot-like connection piece for being fitted into a recess of the reception member.

2. The dental apparatus according to claim 1, wherein the recess of the reception member is formed in an upper wall of a housing of the dental apparatus, the suction line of the suction pump being connected to the recess of the reception member and further to the closure one-way check valve which is accommodated by the spigot-like connection piece.

3. The dental apparatus according to claim 2, wherein a projection which projects upwardly from a bottom portion of the recess of the reception member conditions the closure one-way check valve for being opened by pushing the valve member upwardly into its open position with respect to the valve seat of the connector piece.

4. The dental apparatus according to claim 1, wherein the connection between the connector piece of the fluid reservoir and the recess of the reception member is sealed by at least one sealing ring and is mutually fixed by a spring ring.

5. The dental apparatus according to claim 1, wherein the suction line of the suction pump is provided with a directional control valve by means of which an associated connection line of a dental handpiece which is connected with the pressure line of the suction pump may be alternately connected with two fluid reservoirs that contain different fluids and that are received by two different reception members with which the suction pump is connected with two branches of the suction line.

6. The dental apparatus of claim 5, wherein the dental handpiece may be connected by its associated connecting line and via said directional control valve with a supply line for fresh water.

7. The dental apparatus according to claim 6, wherein a supply of fresh water and/or a supply of fluid from a fluid reservoir may be selectively switched between a first dental handpiece and a second dental handpiece via a first change-over switch valve and a second change-over switch valve which are arranged downstream of the directional control valve in associated connecting lines of the first and second handpieces.

8. The dental apparatus according to claim 7, wherein said first handpiece is a dental scaler for a dental ultrasonic treatment and said second handpiece is a dental abrasive blasting instrument having an integrated powder reservoir and being provided with an associated water supply line and an associated supply line for compressed air for supplying a nozzle piece of the dental abrasive blasting instrument with a combined jet of compressed air mixed with an abrasive dental powder of its integrated powder reservoir and water.

9. A fluid reservoir containing a fluid for being used with a dental apparatus connected with a dental handpiece for dental treatment, comprising a connector piece which is provided with two one-way check valves of which a valve member of a first one-way check valve is arranged over a discharge opening of the fluid reservoir and adapted for being pushed into an open position against a biasing force of a closure spring and relative to a valve seat and of which a valve member of a second one-way check valve is arranged over an aeration opening of the fluid reservoir for balancing a negative pressure which will be produced inside of the fluid reservoir when fluid is drawn from the fluid reservoir in the open position of the valve member of the first one-way check valve, and a cap-shaped cover piece for accommodating the two one-way check valves and adapted for being fixed on its one side to the fluid reservoir for closing a fluid filler opening of the fluid reservoir and for being fitted on its opposite side into a complementary recess of a reception member of the dental apparatus by means of spigot-like connection piece which accommodates the first one-way check valve.

10. The fluid reservoir according to claim 9, wherein the cap-shaped cover piece is provided with an inner thread of a screw-type closure of which a complementary outer thread is provided on a neck portion of the fluid reservoir whereby the outer thread also serves as a screw-on thread of a closure cap for the fluid reservoir.

11. A dental apparatus comprising means for allowing a connection of a fluid reservoir containing a fluid which is supplied to a dental handpiece under control of a valve arrangement by a suction pump which has a suction line that is connected with a reception member of a connector piece of the fluid reservoir, comprising:

a closure one-way check valve which is arranged on the connector piece of the fluid reservoir whereby a valve member which is biased by a closure spring towards a closing position on a valve seat of the connector piece may be pushed by a counterpart into an open position against the biasing force of the closure spring, an areation one-way check valve which is arranged over an aeration opening of the connector piece of the fluid reservoir for compensating a negative pressure which will be produced inside of a fluid reservoir when the closure one-way check valve is opened at its valve member and fluid is drawn from the fluid reservoir via the suction line of the suction pump and supplied to the handpiece via a pressure line of the suction pump; and wherein the suction line of the suction pump is provided with a directional control valve by means of which an associated connection line of a dental handpiece which is connected with the pressure line of the suction pump may be alternately connected with two fluid reservoirs that contain different fluids and that are received by two different reception members with which the suction pump is connected with two branches of the suction line.

12. The dental apparatus of claim 11, wherein the dental handpiece may be connected by its associated connecting line and via said directional control valve with a supply line for fresh water.

13. The dental apparatus according to claim 12, wherein a supply of fresh water and/or a supply of fluid from a fluid reservoir may be selectively switched between a first dental handpiece and a second dental handpiece via a first change-over switch valve and a second change-over switch valve which are arranged downstream of the directional control valve in associated connecting lines of the first and second handpieces.

14. The dental apparatus according 13, wherein said first handpiece is a dental scaler for a dental ultrasonic treatment and said second handpiece is a dental abrasive blasting instrument having an integrated powder reservoir and being provided with an associated water supply line and an associated supply line for compressed air for supplying a nozzle piece of the dental abrasive blasting instrument with a combined jet of compressed air mixed with an abrasive dental powder of its integrated powder reservoir and water.

* * * * *